United States Patent [19]
Alt et al.

[11] Patent Number: 5,954,753
[45] Date of Patent: Sep. 21, 1999

[54] IMPLANTABLE DEFIBRILLATOR WITH IMPROVED TESTING OF CAPABILITY TO DEFIBRILLATE

[75] Inventors: Eckhard Alt, Ottobrunn, Germany; Lawrence J. Stotts, Lake Jackson, Tex.

[73] Assignee: Sulzer Intermedics, Inc., Angleton, Tex.

[21] Appl. No.: 08/874,036

[22] Filed: Jun. 12, 1997

[51] Int. Cl.⁶ .................................................. A61N 1/39
[52] U.S. Cl. .................................................. 607/8
[58] Field of Search .................................. 607/7, 8

[56] References Cited

U.S. PATENT DOCUMENTS

| | | | |
|---|---|---|---|
| 5,105,809 | 4/1992 | Bach, Jr. et al. | 607/8 |
| 5,346,506 | 9/1994 | Mower et al. | 607/7 |
| 5,564,422 | 10/1996 | Chen et al. | 607/8 |

FOREIGN PATENT DOCUMENTS

| | | |
|---|---|---|
| 91113597 | 8/1991 | European Pat. Off. . |
| 93118096 | 11/1993 | European Pat. Off. . |

OTHER PUBLICATIONS

PCT/ISA 220 dated Aug. 31, 1998.
Malkin et al., Estimating Defibrillation Efficacy Using Combined Upper Limit of Vulnerability and Defibrillating Testing, vol. 43, No. 1, Jan. 1996.

*Primary Examiner*—Jeffrey R. Jastrzab
*Attorney, Agent, or Firm*—Schwegman, Lundberg, Woessner & Kluth P.A.

[57] ABSTRACT

A defibrillator is designed for implantation in a patient and for programming certain of its parameters after implantation, including energy content of a shock waveform and timing of delivery of the shock waveform. A shock waveform generator of the device is responsive to a trigger signal for timed production of a shock waveform having a programmable shape and energy content designed for terminating atrial or ventricular fibrillation (AF or VF) of the patient. A detection circuit processes a sensed cardiac signal of the patient to determine the relative timing of various portions of the cardiac signal, including the P-wave and the T-wave. In a test mode of the device, the energy content of a shock waveform is programmed to a magnitude exceeding the upper limit of vulnerability (ULV) of the patient, and the trigger signal times the delivery of a shock waveform of proper magnitude relative to the occurrence of a selected event in the cardiac signal, such as a cardiac stimulus, the P-wave or QRS complex, for application to the patient's heart coincident with the vulnerable period of a P-wave or a T-wave. In a method for testing the capability of the defibrillator to terminate VF, the probable ULV of the patient's heart is determined or estimated, the defibrillator is set to deliver a shock of sufficient energy to exceed the probable ULV, and delivery of the shock is initiated into the vulnerable period of the P-wave or T-wave. The defibrillator is selected with the capacity to deliver a shock of maximum energy exceeding the probable ULV by a margin deemed to provide an adequate safety margin for the patient. The occurrence of the vulnerable period of the P-wave or T-wave is precisely timed from a predetermined event in the patient's cardiac signal.

20 Claims, 3 Drawing Sheets

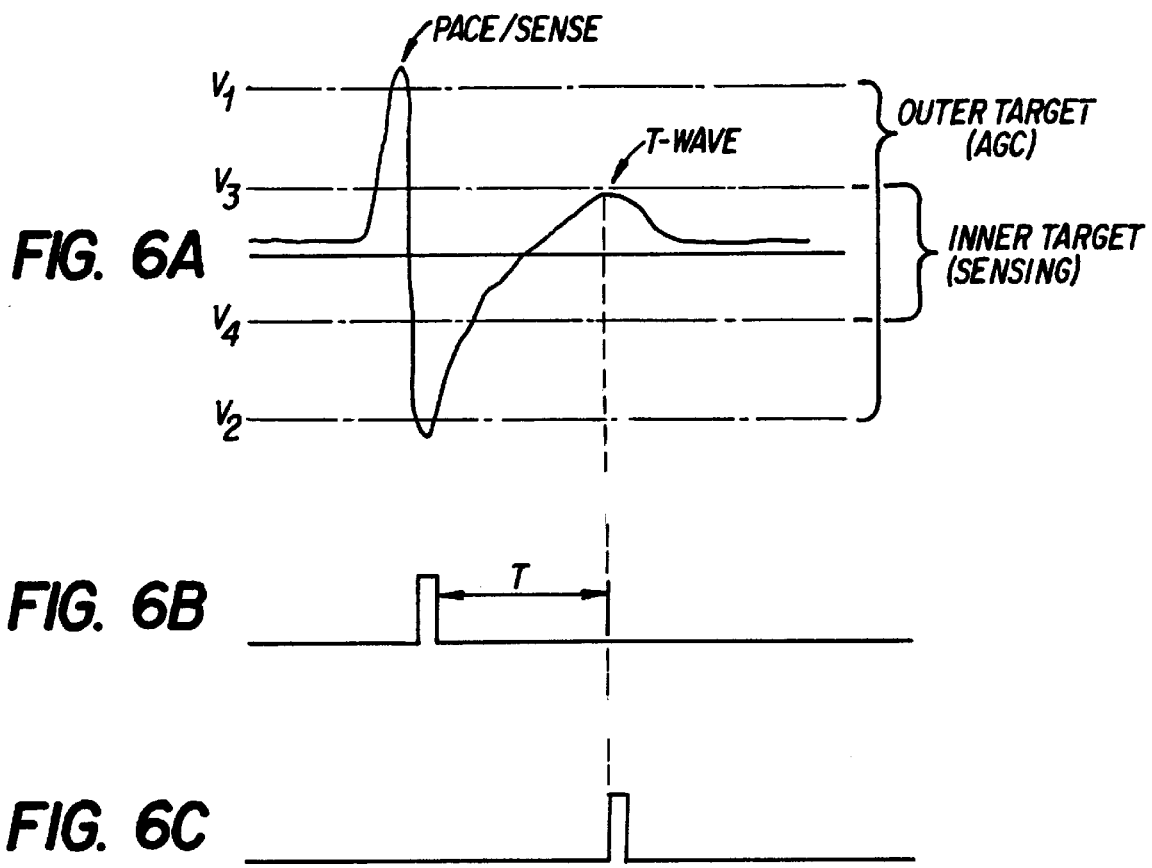

IMPLANTABLE DEFIBRILLATOR WITH IMPROVED TESTING OF CAPABILITY TO DEFIBRILLATE

BACKGROUND OF THE INVENTION

The present invention relates generally to implantable medical interventional devices, and more particularly to improvements in techniques and devices for determining the capability of an implanted cardiac defibrillator to defibrillate the implant patient and to do so with an adequate safety margin.

Considerable progress has been made in recent years in the field of implantable defibrillators, primarily in reduction of device size, weight, and volume attributable to improved electronics, a better understanding of and reduction in defibrillation threshold (DFT), and the consequent use of smaller batteries and capacitors. A major clinical benefit of the reduction in physical characteristics of the defibrillator is that it may be implanted in the pectoral region, in contrast with lower abdominal areas for the bulkier prior art defibrillators. This factor alone has contributed to a marked reduction in the complexity of and time required to perform the implant procedure. Reduced morbidity and fewer complications associated with the pectoral implant procedure has been demonstrated in studies by various practitioners (see, e.g., E. Hoffmann et al., "Chronic Experience with Pectoral Defibrillator Implant," *Pace*, 18: 888A372 (1995)).

Additionally, the use of the so-called "active can configuration," in which the metal housing or case of the device (often referred to as the "can") enclosing the electronics and batteries is used as one of the poles for administering the defibrillating shock, has led to further simplification of the implant procedure for defibrillators. The second pole of the configuration is an endocardial defibrillation electrode or coil on the implanted lead, which is situated in the cavum of the patient's right ventricle when the lead is fully implanted. The combination of reduced size, weight, and volume, along with pectoral implant site, active can configuration, and other improvements have enabled the defibrillator to be implanted in a procedure ranging from sixty to ninety minutes (see, e.g., H. Schmidinger et al., "Learning Effect in Defibrillator Implant Duration," *Pace*, 18: 885A359 (1995)).

One of the applicants herein has developed and performed an implant procedure which is even faster and less risky, with the patient subjected only to a local anesthetic and sedation. In this procedure, it is not necessary to administer a general anesthesia intubation narcosis, which represents a considerable advantage for patients with reduced myocardial function, characteristic of the majority of candidates for an implantable defibrillator. Consequently, a major risk of further reducing an already lowered cardiac output in patients who are prime candidates for the procedure, attributable to inhalative narcotics used in general anesthesia, is avoided. Use of local anesthesia and a short action sedation such as versed or propofol for the time during which the shock is applied has further reduced morbidity and mortality of the implant procedure.

Despite these improvements, the technique typically used to test the capability of the implanted device to defibrillate is a debilitating and all too often deadly procedure for the patient. At least two and often three or more DFT determinations are made—by repeatedly inducing ventricular fibrillation (VF) through such means as fast ventricular stimulation, or by applying 50 or 60 Hertz (Hz) alternating current or a T-wave shock, after which the VF is sought to be terminated by a defibrillating shock is delivered to the ventricular mass by the implanted device. The predetermined energy level of the shock is calculated to provide a safety margin of about 10 joules, which is usually deemed sufficient to assure termination of the VF in even the worst cases, namely, where a high ventricular DFT is present and/or where the VF is a certain type which is very difficult to terminate. Nevertheless, the uncertain nature of fibrillation makes the repeated inducement and termination of VF an important confidence builder for the implanting physician, that the implanted device will consistently provide a safe and effective therapy to defibrillate the patient's heart.

Testing by repetitive inducement of VF is used not only during the initial implant procedure, but also in pre-hospital discharge testing and in patient follow-up visits to the physician. Shocks of adequate energy content, field strength, and vectoral component will usually defibrillate. During the procedure, the intracardiac or surface EKG signal is monitored by telemetering to a programming console or display terminal, or by strip-chart recording. Although it is important for the implanting physician to be satisfied that the device will operate as intended, the testing procedure has been the greatest risk to patient survival during an implant, notwithstanding that for determining DFT the energy delivered to terminate is typically successively lowered for the repetitions. The concern for survival is greatest for patients with enlarged heart and compromised myocardial function, such as an ejection fraction in a range below 25 percent. Transesophageal echocardiographic measurements, determination of enzymes, measurement of pulmonary wedge pressure, and radionucleide studies have shown that even after one shock, the end diastolic volume of the ventricle increases and the ejection fraction decreases, adding to the risk. Further severe risk is present for patients under antiarrhythmic drug treatment at times when VF is being induced in connection with the implant procedure. Further reduction of an often compromised myocardial function is an outcome, which may lead to a critical drop in blood pressure, prolonged operating time, and unwanted increase in intrinsic catecholamine stimulation.

Accordingly, it is a principal aim of the present invention to provide an improved method and technique for testing the capability and efficacy of a defibrillator which is in process of being implanted, or which already has been implanted in the patient, to terminate an episode of ventricular fibrillation, and to do so in a way that offers markedly reduced risk to the physical well-being of the patient.

SUMMARY OF THE INVENTION

According to the invention, an improved technique and device that avoids the repetitive defibrillation trials while still affording the implant physician sufficient confidence that the implanted defibrillator will safely terminate fibrillation is based on the upper limit of vulnerability (ULV) of the patient to fibrillation. Normally, a shock applied during occurrence of the T-wave will induce fibrillation because the region around the peak of the T-wave constitutes a vulnerable period. A shock having a magnitude up to a certain strength (viz., at least ten times the pacing threshold) will cause the heart to go into fibrillation. But if a certain shock strength is exceeded, VF is no longer induced. Animal measurements have shown good correlation between shocks applied at certain times within the T-wave and the patient's defibrillation threshold or DFT. The reader is referred, for example, to three abstracts published in the *American Heart Journal* of September 1994, 128, 3:632, namely:

Karagueuzian, H. S. et al., "The Relation Between Propagated Graded Responses to Vulnerability and Defibrillation: A Hypothesis"; Chen, P. S. et al., "The Upper Limit of Vulnerability and the Defibrillation Threshold"; and Idriss, S. F. et al., "Effect of Rapid Pacing and T-wave Scan on Upper Limit Defibrillation Estimate".

The invention provides an improved method for testing the capability of a defibrillator implanted in a patient to terminate VF by application of a defibrillating shock to the heart with an adequate margin of safety measured by the strength of the shock relative to the maximum energy capacity of the defibrillator. A lead is implanted for applying shocks to the patient's heart. The defibrillator is then at least partly implanted in the patient and connected to the lead. A shock delivered from the device to the lead has an energy level exceeding the patient's predetermined ULV (which may be known or merely estimated or predicted by the physician ), and is applied directly into the vulnerable period of the T-wave. The energy level of the shock, although above the ULV, is set sufficiently below the maximum energy capacity of the defibrillator to meet a margin of safety deemed by the physician to be adequate. During the procedure the patient's cardiac function is monitored.

Delivery of the shock is initiated at a point in time which is a predetermined interval after occurrence of a selected detectable event in the signal, such as the occurrence of the T-wave representing the repolarization following a spontaneous or paced beat, or of the T-wave following a QRS complex. Preferably, the defibrillator has the capability to determine the instant of time at which the shock is to be delivered, by calculation of the time interval from the prescribed event in the detected intracardiac signal.

Preferably, the defibrillator is caused to apply the shock to the lead automatically at that instant of time, by physician-programming of the defibrillator in a test mode corresponding to the implant procedure mode, pre-hospital discharge checkup mode, and/or patient follow-up mode.

In an alternative version of the method, the capability of the implantable defibrillator to terminate VF is tested by determining the probable ULV, setting the defibrillator to deliver a shock of sufficient electrical energy to exceed the determined probable ULV, and delivering the shock into the vulnerable period. The selected defibrillator should possess the capability to deliver a shock of maximum energy exceeding the determined probable ULV by an amount which the physician deems to provide an adequate safety margin for the patient. The timing of the vulnerable period of the T-wave is precisely determined relative to the designated event in the patient's cardiac signal. As with the preferred method, the alternative method is performed during the implant procedure, at the patient checkup procedure in conjunction with discharging the patient from the hospital after the implant, and/or at the patient follow-up procedure at the physician's office.

An improved implantable programmable defibrillator device includes means for verifying that the energy in the shock waveform may be programmed to a level sufficiently high to assure that the device is capable of terminating ventricular fibrillation by generating a shock waveform with energy content exceeding the patient's upper level of vulnerability, and that the shock is precisely timed to coincide with the vulnerable period of the T-wave in the intracardiac signal. The latter function is achieved by programming the timing of the shock waveform so that the shock will be delivered at an instant within the vulnerable period, at a precise time interval after a predetermined detectable event has occurred in the intracardiac signal, e.g., the occurrence of the T-wave representing the repolarization following a spontaneous or paced beat, or the T-wave following a QRS complex.

An alternative implantable device is programmable with respect to certain of its parameters, including energy content of the shock waveform, and timed delivery of the shock waveform, after implantation in the patient. Shock waveform generating means is responsive to a trigger signal for timed generation of a shock with programmed shape and energy content, and detection circuit means processes the sensed cardiac signal to determine the relative timing of various portions thereof, including the P-wave, the QRS complex, and the T-wave. Test mode means is available to program the energy content of the shock waveform to a magnitude exceeding the upper limit of vulnerability of the patient, and to trigger the timing of the shock relative to the occurrence of the selected event in the cardiac signal, for application to the patient's heart coincident with the vulnerable period of the T-wave.

The test mode means produces the trigger signal for timing the production of a shock of the necessary magnitude to occur at a specified time following a P-wave, or following occurrence of a Q-wave or a QRS complex, or following the delivery of a pacing stimulus.

The implantable programmable defibrillator includes means for determining precise timing of the T-wave in the intracardiac signal following a designated detected event in the intracardiac signal, such as a spontaneous or paced beat, or the occurrence of a QRS complex; and means responsive to a programmed test mode of the device for delivering a shock programmed to exceed the upper limit of vulnerability of the patient's heart at a point in time coinciding with the vulnerable period of the T-wave, to assure that the DFT is met, while maintaining an energy reserve that establishes a predetermined adequate safety margin for the defibrillator.

BRIEF DESCRIPTION OF THE DRAWINGS

The above and still further aims, objects, aspects, features and attendant advantages of the present invention will become apparent from a consideration of the following detailed description of the best mode currently contemplated for practicing the invention, encompassed by certain preferred methods and embodiments, taken in conjunction with the accompanying drawings, in which:

FIGS. 6A, 6B, and 6C illustrate exemplary signals appearing at various points in the circuit of FIG. 5, useful in explaining the operation of the circuit and the timing and delivery of the shock to the heart.

DETAILED DESCRIPTION OF THE PREFERRED METHODS AND EMBODIMENTS

Figure 1:
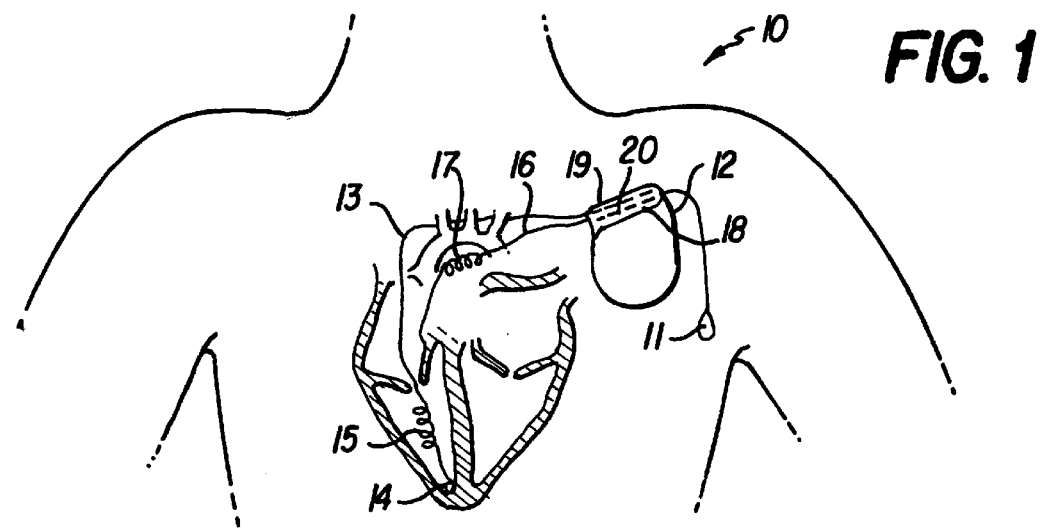
FIG. 1 is a partial phantom view of a patient in which a defibrillator of the invention is implanted pectorally.

In FIG. 1, a patient 10 has a defibrillator with a metallic case 12 implanted in the pectoral region. A transvenous lead 13 electrically connected at its proximal end to the defibrillator (or to be so connected) is inserted through the superior vena cava, the right atrium (RA), the tricuspid valve, and into the right ventricle (RV), to position a pacing electrode 14 at the distal tip of lead 13 at the apex of the RV. The pacing electrode is positioned in firm contact with the myocardium for the purpose of stimulating the heart when pacing pulses are delivered thereto, and sensing the intracardiac potentials at other times. To that end, the electrically conductive wire for the pacing electrode 14 is connected to the output node(s) of a pacing pulse generator (not shown) of the defibrillator, as well as to the input node(s) of a sense amplifier and related detection processing circuitry (not shown) of the pacing circuit of the defibrillator, with appropriate conventional switching or other isolation means to preclude interference between the two functions.

A defibrillation electrode in the form of a coil 15 on lead 13 is disposed relative to the distal tip of the lead to be positioned in the right ventricle when the pacing electrode 14 is positioned at the apex of the RV, as shown in the configuration of FIG. 1. When a shock is delivered to the heart from the implanted defibrillator, it is applied preferably between (i.e., across) the coil electrode 15 and the metallic case 12 of the defibrillator. Alternatively, the shock may be applied between the coil electrode 15 and a second defibrillation coil electrode 17 on a lead 16 which is also electrically connected to the defibrillator. If coil electrode 17 is used, lead 16 may be inserted in the vascular system so that the coil 17 resides in either the superior vena cava, or the left subclavian vein. The female connectors 19, 20 in the header 18 of defibrillator case 12 make good electrical contact to the respective proximal ends of leads 13 and 16.

An additional subcutaneous lead 11 is used both for shocking the heart and sensing the ECG, this lead being connected to the defibrillator by the connector block in header 18 and a terminal thereof. The two coil electrodes 15 and 17 are connected by their respective wires through leads 13 and 16 to the output stage of a conventional switched storage capacitor circuit or capacitor bank of the implanted defibrillator, so that a predetermined shock waveform can be supplied to the selected poles after detection of VF by the sense circuit.

Figure 2A:
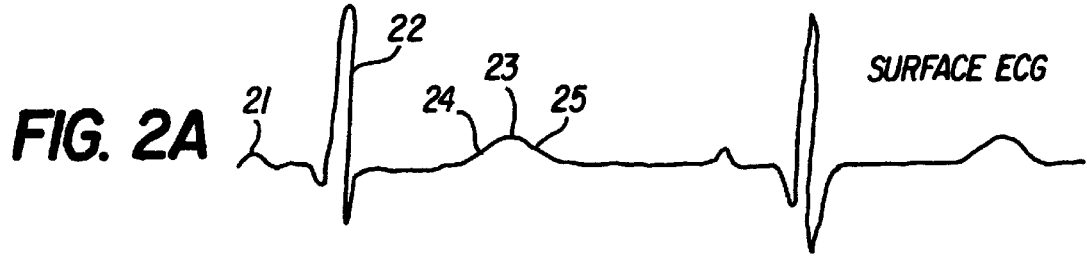
FIGS. 2A, 2B, and 2C are signal waveforms indicative of cardiac activity at various detection points.
Figure 2B:
Figure 2C:
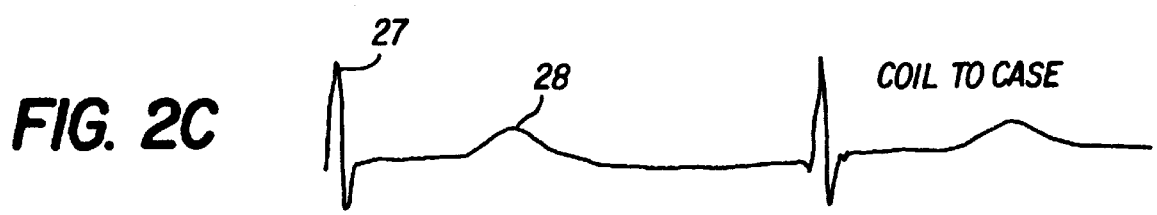

The cardiac activity signal detected at various points on or in the patient's body is illustrated in FIG. 2, including a surface electrocardiogram (ECG) in FIG. 2A, and intracardiac waveforms for the tip-to-coil and the coil-to-case points of detection by the sense circuitry of the defibrillator in FIGS. 2B and 2C. In the surface ECG tracing of FIG. 2A, or the corresponding ECG derived between case 12 and subcutaneous lead 11, the P-wave 21, QRS complex 22, and T-wave 23 are evident, the T-wave correlating to repolarization of the ventricle with a region of increasing slope 24 and another of decreasing slope 25. In contrast, the intracardiac signal taken from tip electrode 14 to coil electrode 15 in FIG. 2B is characterized by a relatively greatly reduced T-wave, and a ventricular QRS complex 26 which is much narrower than that of the surface ECG. This is because FIG. 2B primarily represents a local depolarization at the point where the tip electrode 14 makes contact with the myocardium.

In the coil-to-case situation of the intracardiac signal of FIG. 2C, the QRS complex 27 is broader than that of either of the other two cardiac activity tracings, and has a more dominant T-wave 28. An even closer correlation of the intracardiac signal to the surface ECG of FIG. 2A is achieved by use of the coil electrode 15 as one pole, and the coil electrode 17 and defibrillator case 12 together as the second pole, especially in the duration of the QRS complex and the morphology and timing of the T-wave. This is because that configuration is more representative of the true global depolarization and repolarization of the ventricle rather than the more local phenomenon of either bipolar tip to coil of FIG. 2B or the coil to coil situation of FIG. 2C.

Figure 3:
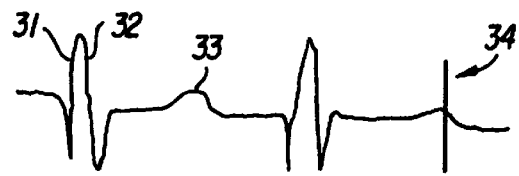
FIG. 3 is an illustration of the morphology or pattern of the intracardiac signal which occurs with pacing stimulation.
Figure 4:
FIG. 4 is a an illustration of the cardiac waveform for VF.

A more significant change in the morphology of the intracardiac signal occurs with stimulation, as shown in FIG. 3. Here, a pacing stimulus occurs at 31, a broadened QRS complex at 32, which normally represents a left-bundle-branch block following stimulation in the apex of the right ventricle, and a representative T-wave at 33. A shock 34 applied into the T-wave with energy content below the ULV will induce VF as shown in FIG. 4. As FIG. 4 illustrates, the VF is not merely entirely random, but has a certain cyclical morphology, frequency content, and amplitude, as indicated at 41 which focuses on the larger fibrillation cycle amplitudes, and at 42 which represents the smaller fibrillation cycle amplitudes.

In general, as measurements of the event have shown, the amplitude of the VF waveform ranges between 50% and 70% of the sinus rhythm intracardiac potential. If the amplitude of the R-wave during sinus rhythm is sufficient to be detected, and particularly if the slew rate of the signal— rated in millivolts per millisecond (mV/ms)—is such that the maximum increase in that signal's amplitude over time is in a range of about 0.7 to about 1.0 mV/ms, then detection of fibrillation is assured. Thus, it is unnecessary to induce fibrillation purely for the sake of determining the sensing capabilities of the defibrillator during VF.

According to the present invention, the occurrence of a T-wave is automatically determined after a spontaneous or a paced beat, or after some other periodic detectable event in the intracardiac signal. Preferably, a sequence of from 4 to 8 paced beats is applied at a rate above the intrinsic rate. During those beats of elevated rate, the device automatically determines the precise time of occurrence of the T-wave relative to a selected detectable event in the intracardiac signal, preferably the delivery of the pacing stimulus.

Figure 5:
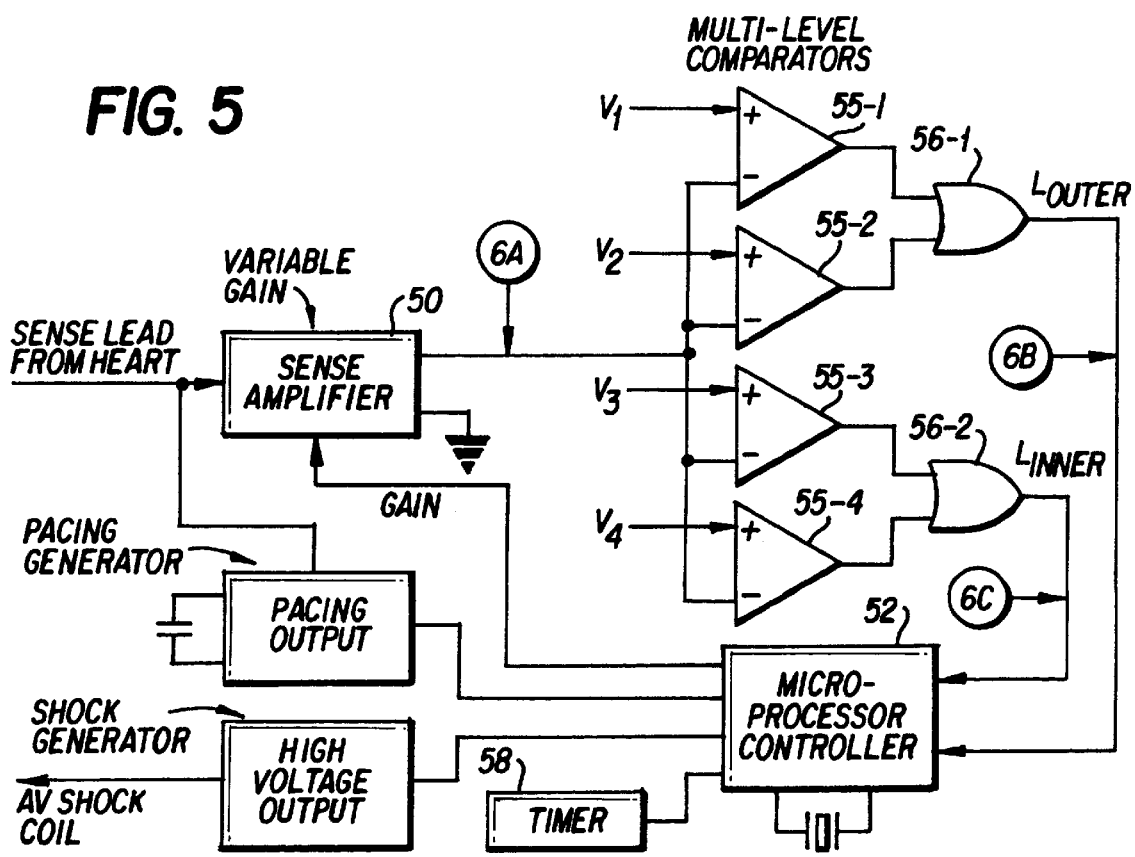
FIG. 5 is a block diagram of a logic circuit for precisely timing occurrence of the peak of the T-wave relative to a cardiac event such as a spontaneous or paced beat, and for delivering the shock waveform into the vulnerable period.

In the circuit of FIG. 5, a sense amplifier 50 receives the intracardiac signal 10 from the sense lead/electrode in the heart. The sense amplifier has a variable gain which is controlled by a gain input from a microprocessor controller (or microcontroller) 52, and operates to amplify and filter the signal from the heart. The output signal from the sense amplifier 50 is illustrated in FIG. 6A. An outer target for the automatic gain control (AGC) is represented by the outer voltage limits V1 and V2, and an inner target for sensing is represented by the inner voltage limits V3 and V4. The pace/sense and T-wave occurrences are as shown in the Figure.

The output signal of FIG. 6A is applied to a plurality of multi-level voltage comparators 55, specifically four comparators, two of which 55-1 and 55-2 are associated with the outer target and have reference voltages V1 and V2 applied to their respective+inputs. The other two comparators 55-3 and 55-4 are associated with the inner target and have reference voltages V3 and V4 applied to their respective+inputs. The other (−) input of each of the four comparators is the output signal of sense amplifier 50. Thus, the voltage comparators indicate crossings of the inner and outer targets by that signal, and together with associated gates 56-1 and 56-2, generate respective $L_{OUTER}$ and $L_{INNER}$ logic signals which are fed to the microcontroller 52. These logic signals for $L_{OUTER}$ and $L_{INNER}$ are illustrated in FIGS. 6B and 6C, respectively, and are self-explanatory.

The software AGC algorithm includes non-pacing and pacing functions. In the former, the gain is increased if in two consecutive cycles the sense (inner) target is crossed and the AGC (outer) target is not crossed, and the gain is decreased if in one cycle the AGC target is crossed. In the pacing function, the gain is increased and decreased to dither around the T-wave. With this approach, the peak of the T-wave will just cross the sense (inner) target when pacing. During sensing, the T-wave moves below this level and is not sensed. Pacing stabilizes the location of the T-wave. A timer 58 is used to measure the time interval, t, between a pace and the T-wave, as shown in FIG. 6B. Finally, the microcontroller receives a timing signal as in FIG. 6C to trigger the delivery of a shock into the T-wave.

The logic automatically selects the best lead to determine and precisely time the occurrence of the T-wave, from the plurality of internal leads available for detection purposes. Conventional signal processing means such as zero-crossing or peak level detection are used to determine the delay of the peak wave occurrence after the application of the paced beats. This value is then used to adjust the application of a high energy shock selected according to the desired safety margin. For example, if the defibrillator has a capacity or output rating of 25 joules, such as using a 75 microfarad ($\mu$F) capacitor charged to 850 volts (V), a safety margin of 10 joules is deemed to be adequate. Thus, a shock having an energy content of 15 joules, if sufficient to exceed the ULV of the patient—as it would in virtually every case—should be capable to defibrillate the heart, and is suitable to demonstrate the capability of the device to perform its therapy function on the patient.

As in the case of the typical DFT-determination method of the prior art, more than one shock should be applied. But in the case of the present invention, the shocks are not repeated to terminate VF which has been induced. Instead, if the patient does not go into fibrillation (except as may occur virtually instantaneously with subsequent defibrillation from one and the same shock), the number of shocks is reduced by at least half and probably more. Preferably, two shocks are delivered with slightly different time delays relative to the event of interest such as the occurrence of a spontaneous or paced beat. For example, each shock may be delivered before the peak of the T-wave, one at say 50 ms ahead of the peak, and the other at 30 ms ahead of the peak of the next T-wave. This constitutes an indirect determination of the DFT although that value is not used for any particular purpose in the present invention.

T-wave shocking may be analyzed with respect to the patient's ECG. The cell membrane potential is measured in millivolts, and if the resting potential is –30 mv, followed by a zero value, a+30 mv, and a value of 100, the depolarization starts very rapidly at or near –30 mv, undergoes an overshoot past 100 mv, proceeds toward a flattened region, and then decreases gradually and more rapidly toward the resting potential of the cell. The individual cell's status correlates with the ECG which is a summary of activity of all of the individual cells.

Within each individual cell there is a certain phase of absolute refractoriness, and during that phase, virtually any kind of shock may be applied to the cell without significant effect. The shock may have a low energy value, or a high energy value, but will not induce anything. Following the absolute refractory period, a relative refractory period commences. If a shock is applied in the relative refractory period, the response once again is that the cell depolarizes, but in a considerably different manner from the earlier depolarization. In particular, the upstroke is slower and the maximum value achieved is lower, but in any event there is a membrane potential in this phase. But to induce something here requires a higher energy shock than before (prior to the refractory phase). So a very sensitive window exists which means that if a shock is applied in the relative refractory phase, it may induce fibrillation because the cells are in different status—some are in the earlier status, some are in the later status, and so forth.

In that phase, the effect of the shock depends to a large extent on the amount of energy applied. If a shock of 0.5 to 6.0 joules is applied, fibrillation will likely be induced. But if higher energy shocks are applied, fibrillation is temporarily induced but is immediately halted. In other words, fibrillation and defibrillation occur at virtually the same instant—with the same shock. The region beginning near the peak of the T-wave and ending shortly thereafter is the vulnerable period, and this avoidance of fibrillation—or at least its termination coincident with its inducement occurs at the upper limit of vulnerability (ULV). It has been found that the ULV matches well with the defibrillation threshold (DFT). A patient may have a DFT of 15 joules—which means that he or she needs a 15 joule shock to halt fibrillation. A shock with a strength of or greater than 15 joules, for example, which is applied to the T-wave in the vulnerable period will no longer induce fibrillation because it induces and halts it at the same time. When a 12 joule shock is applied into the T-wave, it may act as a fibrillation-inducing T-wave shock. But if a 15 joule shock is applied into the T-wave without inducing fibrillation, the physician knows that this is at or near the DFT, without putting the patient at risk of fibrillation. For practical purposes, with most patients it is undesirable to go through all of the threshold testing, when it is really only desired to know whether the device will halt fibrillation and provides a sufficient safety margin for the patient.

The invention makes it only necessary to apply one or two (preferably, two) T-wave shocks of sufficient strength to indicate that it is (or they are) at the ULV, and thus, at the DFT, and that the device has a maximum energy rating to provide sufficient safety margin. The patient is not put at any true risk of fibrillation, because fibrillation is halted as soon as it is induced—at the same instant of time—and is unlikely to even show up in the surface EKG.

Of course, the implanting or follow-up physician could step the energy content or strength of the shock downwardly (i.e., decrement the shock) with succeeding shocks until a shock were found to induce fibrillation without termination, in order to obtain a more precise indication of the patient's DFT and ULV, but that is not really the point of interest. Rather, it is knowing that the device to be implanted can terminate fibrillation and provides an adequate safety margin for the patient in whom it is being implanted.

The critical aspect of the T-wave shock will be recognized as the timing. If a shock is applied in the period of absolute refractoriness, i.e., is applied early, it would not induce fibrillation and, since it is outside the critical window, could be misinterpreted as a successful test and demonstration that the DFT was met with adequate safety margin in the device. In fact, however, the test was defective as it was not a timely delivery of the shock, and has demonstrated nothing. Hence, knowledge that will enable proper timing of the T-wave shock is most critical to assure accuracy and confirmation of the test.

To arrive at the proper timing, the test is oriented upon the T-wave. It is known that the most sensitive timing window occurs at the peak of the T-wave. Therefore, a fixed coupling can be obtained for the particular patient. In that regard, each patient has a different pattern—the interval from the Q-wave to the T-wave differs from patient to patient, depending on medication, beta blockers, potassium levels, and so forth, in a range from about 250 to about 350 milliseconds (ms). As noted above, if a fixed T-wave shock coupling interval is used, the correct point for shocking might well be missed, and the results are likely to be misinterpreted. It is critical, then, to identify the vulnerable period of the T-wave by its timing after a Q-wave or QRS complex or after a pacing stimulus. The variation from patient to patient makes it difficult to predict the occurrence on a fixed basis. Preferably, the shock is applied a certain percentage of the QT time interval prior to the peak of the T-wave, such as about 10% or approximately 30 ms.

If an automatic measurement of the T-wave is not achievable with a particular device, the timing of occurrence of the T-wave must be arrived at outside the patient. In that situation, it is necessary to determine from the ECG with a ruler the approximate number of milliseconds that have elapsed before occurrence of the T-wave peak (or onset) measured from the base point of the Q-wave or a stimulus (e.g., 270 ms, or 320 ms, for example). An added difficulty with this is that the outside (surface) ECG does not provide timing information as precise as that inside the heart (the intracardiac signal) relative to the base point, so better accuracy is achieved by detecting the intracardiac waveform and by telemetry, using it to arrive at the T-wave timing measurement. Then the T-wave shock is programmed in ms to occur at the desired point in time relative to the base point.

The better procedure remains for the device itself to determine the actual timing of the T-wave and thus, of the shock delivery, for the patient in question, to avoid the possibility of human error. In the case of the present invention, the device is programmed with an implant procedure (and pre-hospital discharge and follow-up procedure) in which the device determines the timing for delivery of a T-wave shock and the magnitude of the shock is set according to the physician's prediction of the magnitude of the ULV (and DFT) and selection of a desired safety margin for the device being implanted (or which has been implanted, in the case of the checkout or follow-up procedure).

This is also in keeping with the trend toward greater use of the device itself for testing purposes rather than going through an external device. The device is implanted in the pocket made by incision in the pectoral region, for example, but before the wound is closed, the tests are conducted. Of course, a problem exists that if the device is subjected to too much testing with its own internal capabilities, e.g., threshold testing and so forth, the battery may be discharged to a point that makes it incapable of meeting the desired longevity of the device in actual use. The present invention assists in that regard as well, since it reduces the number of shocks required to be delivered from the device, at least for this part of the test procedure. Rather than repetitively generating shocks whose only purpose is to induce fibrillation, followed in each instance of an induction shock by a defibrillating shock, only one or, better, two shocks are necessary to assess the capability of the device to properly serve the needs of the patient in whom it is being implanted. And primarily, this also reduces the physical risks to the patient in terms of further deterioration of the cardiac function with each episode of fibrillation, and even the risk of patient inability to survive the implant procedure itself. Some studies using transesophageal echocardiogra-phy have shown that repeated induction of fibrillation produces progressive increases in the size and volume of the heart, reduces the contraction capability, and thus lowers the stroke volume. This translates into lowered blood pressure and cardiac output. Each episode of fibrillation increases the size of the heart and weakens cardiac function, with concomitant increased difficulty to defibrillate; and at some point the patient's heart may not be made to resume a regular rhythm from a fibrillating status. Most patient deaths occurring in the defibrillator implant procedure are attributable either to infection following complications of the operation or to intractable ventricular fibrillation.

While the invention has been described in terms of the occurrence of ventricular fibrillation and T-wave shocking, it will be understood that exactly the same mechanisms hold true for P-wave and atrial fibrillation and defibrillation.

Although a best mode currently contemplated for practicing the invention has been described herein, in terms of certain preferred methods and embodiments, it will be recognized by those skilled in the art of the invention that variations and modifications of the disclosed methods and embodiments may be made without departing from the true spirit and scope of the invention. Accordingly, it is intended that the invention shall be limited only by the appended claims and the rules and principles of the applicable law.

What is claimed is:

1. A method for performing a test of the capability of an implantable defibrillator to effectively terminate fibrillation of a patient's heart with adequate safety margin determined by the maximum electrical energy shock available from the defibrillator compared to the actual energy of a delivered shock, comprising the steps of:

determining the vulnerable period of the patient's EKG signal by detecting the precise occurrence of the T-wave in the patient's EKG signal, and delivering a test shock into the vulnerable period of the T-wave without inducing ventricular fibrillation, to confirm that the defibrillation threshold for the patient is met with a predetermined adequate safety margin without further need for threshold testing except as a consequence of having delivered said test shock with an energy content below a level capable to induce ventricular fibrillation.

2. The method of claim 1, wherein said test shock has an energy content a preset number of joules below said maximum electrical energy shock available from said defibrillator.

3. The method of claim 2, wherein said test shock has an energy content at least sufficiently high to induce ventricular fibrillation which is in a range above the patient's lower limit of vulnerability.

4. The method of claim 3, wherein said test shock has an energy content in a range between 2 joules and 15 joules.

5. The method of claim 4, wherein the lower is the energy content of the test shock toward a level which will not induce VF, the higher is the safety margin of the defibrillator.

6. A method for testing the capability of a defibrillator which is to be implanted in a patient to successfully terminate ventricular fibrillation (VF) of the patient's heart by delivery of a test shock from the defibrillator to the heart, with a preselected adequate margin of safety based on the ratio of the energy in the test shock to the maximum energy capacity of the defibrillator, said method comprising the steps of:

implanting a lead in the patient for applying electrical shocks to the heart;

at least partly implanting the defibrillator in the patient and electrically connecting the defibrillator to the lead; and during the vulnerable period of the T-wave, delivering a test shock from the defibrillator to the lead of predetermined energy level exceeding a minimum that could induce VF, but sufficiently below said maximum energy capacity of the defibrillator to provide said preselected adequate margin of safety, while monitoring the patient's cardiac function to assess an absence of VF from said test shock as being indicative that said test shock has at least sufficient energy to successfully defibrillate the patient's heart in VF.

7. The method of claim 6 wherein said test shock is selected to deliver an electrical energy level to the heart via said lead which is sufficient to dispense with a need for further testing of capability to defibrillate.

8. The method of claim 6 wherein said test shock is the only test shock delivered to the patient's heart from said defibrillator during performance of said method.

9. The method of claim 6, wherein said test shock has an energy level approximately 10 joules below said maximum energy capacity of said defibrillator.

10. The method of claim 9, wherein said test shock has an energy level not exceeding 15 joules, but at least sufficiently high to induce VF which is in a range of the patient's lower limit of vulnerability.

11. The method of claim 10, wherein said test shock has an energy content in a range between 2 joules and 15 joules.

12. The method of claim 10, wherein the lower the energy content of the test shock in a direction of the lowest level shock from the defibrillator capable of inducing VF when delivered into the patient's vulnerable period without inducing VF, the higher is the safety margin of the defibrillator.

13. A method for performing a test of the capability of an implantable defibrillator to effectively terminate ventricular fibrillation (VF) of a patient's heart with adequate safety margin, where safety margin is a function of comparison of maximum energy level electrical shock available from the defibrillator and actual energy level of a delivered shock, said method comprising the steps of:

delivering a test shock from said defibrillator into the vulnerable period of the T-wave of the patient's cardiac signal, wherein said test shock is preset at an energy level greater than the minimum energy level that will induce VF, and monitoring the patient's cardiac signal to detect an absence of VF following said delivered test shock, whereby to confirm that the defibrillator is capable of terminating VF with a predetermined adequate safety margin.

14. The method of claim 13 wherein said test shock exceeds said minimum energy level by an amount sufficient to terminate VF.

15. The method of claim 14 wherein said test shock is sufficiently below said maximum energy level of the defibrillator to provide said predetermined adequate safety margin.

16. An implantable defibrillator with a capability to effectively terminate ventricular fibrillation (VF) by application of an electrical shock to the patient's heart with adequate safety margin according to the difference between the selected actual energy content of an electrical shock having such capability and the maximum available energy content for an electrical shock from said defibrillator, comprising:

means for testing the capability of the defibrillator to effectively terminate VF with said adequate safety margin without inducing VF during the test procedure, said testing means including:

means for determining the vulnerable period of the patient's EKG signal by detecting the precise timing of occurrence of a T-wave in the EKG signal following a preselected periodic event in the EKG signal, and means responsive to determination of the timing of said vulnerable period for delivering an electrical shock into said vulnerable period, wherein said electrical shock has an energy content which is selected to be at least marginally greater than an estimated minimum level of energy in an electrical shock sufficient to terminate VF in only one shock application, while maintaining at least said adequate safety margin, and means for determining that said delivered electrical shock of said selected energy content has a high probability of effectively terminating VF from a finding that said delivered electrical shock did not induce VF in the patient's EKG signal.

17. The implantable defibrillator of claim 16, wherein said delivered electrical shock has an energy content approximately 10 joules below said maximum available energy content for an electrical shock from said defibrillator.

18. The implantable defibrillator of claim 16, wherein said delivered electrical shock has an energy content not exceeding 10 joules, but at least sufficiently high to induce VF which is in a range above the patient's lower limit of vulnerability.

19. The implantable defibrillator of claim 16, wherein said delivered electrical shock has an energy content in a range between 2 joules and 15 joules.

20. The implantable defibrillator of claim 19, wherein the lower the energy content of the delivered electrical shock toward 2 joules without inducing VF, the higher is the safety margin of the defibrillator.

* * * * *